United States Patent [19]

Patchell et al.

[11] 4,135,021
[45] Jan. 16, 1979

[54] NET-LIKE PRODUCT PRODUCED BY STRETCHING A FILM COMPOSED OF TWO INCOMPATIBLE POLYMERS

[75] Inventors: Albert G. Patchell, Welwyn Garden City; William O. Murphy; Ronald Lloyd, both of Sawbridgeworth, all of England

[73] Assignee: Smith & Nephew Plastics Ltd., Hertfordshire, England

[21] Appl. No.: 696,370

[22] Filed: Jun. 15, 1976

[30] Foreign Application Priority Data

Jun. 16, 1975 [GB] United Kingdom ............... 25659/75

[51] Int. Cl.² .................. A61L 15/00; B29D 7/24; B32B 3/10; B32B 5/02
[52] U.S. Cl. ............................ 428/134; 128/290 W; 264/284; 264/289; 264/DIG. 47
[58] Field of Search ....... 264/147, 284, 289, DIG. 47; 28/DIG. 1; 428/134, 136, 167, 294; 128/290 W

[56] References Cited

U.S. PATENT DOCUMENTS

| 3,496,260 | 2/1970 | Guenther et al. ................ 264/147 |
| 3,550,826 | 12/1970 | Salmela ...................... 264/DIG. 47 |
| 3,746,607 | 7/1973 | Hormon et al. .................. 428/167 |
| 3,922,329 | 11/1975 | Kim et al. ......................... 264/147 |
| 3,954,933 | 5/1976 | Rasmussen ....................... 264/147 |
| 3,969,562 | 7/1976 | Suzuki ............................ 428/155 |
| 4,056,639 | 11/1977 | Schwarz ..................... 264/DIG. 47 |

*Primary Examiner*—J. C. Cannon
*Attorney, Agent, or Firm*—Sprung, Felfe, Horn, Lynch & Kramer

[57] ABSTRACT

A net formed integrally of blended incompatible polymers, with parallel smooth longitudinal ribs interconnected by a plurality of split strands non-uniformly interspersed with a plurality of differently sized voids, by stretching a film with a generally longitudinal set of parallel primary grooves and a transverse or angled set, on the other surface, of parallel secondary grooves.

10 Claims, 1 Drawing Figure

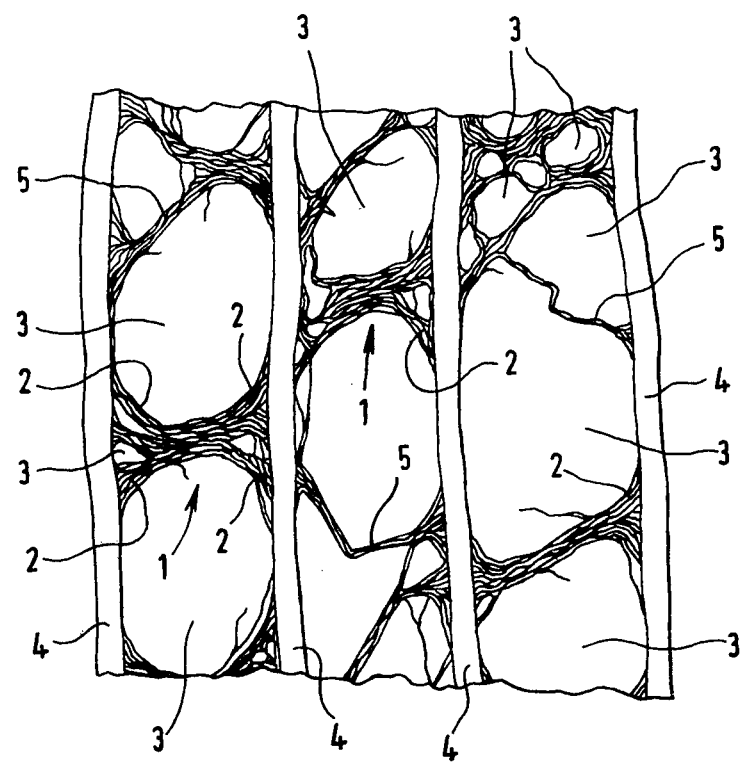

NET-LIKE PRODUCT PRODUCED BY STRETCHING A FILM COMPOSED OF TWO INCOMPATIBLE POLYMERS

This invention relates to a net-like product of synthetic polymeric material and to a process of making such net-like product.

Nets have been made from synthetic polymeric material for many years, either by a process involving an oscillating circular die or by a process involving stretching a profiled polymer sheet. Such materials are not usually of themselves textiles since their appearance and handle are unsuitable for this purpose. Thus, they are usually somewhat lustrous and synthetic looking, and they have a somewhat rough surface. Hitherto, therefore, they have been proposed for example as stiffening layers in made-up garments, or as substrates in, for instance, surgical dressings or pressure-sensitive adhesive tapes.

Prior proposals have suggested nets to constitute a component layer, more especially a cover layer, for absorbent structures such as sanitary towels, disposable diapers or incontinence pads.

One prior proposal is described in U.S. Pat. No. 3,746,607. A sheet of polymeric material is provided either with longitudinal ribs only, or with both longitudinal and transverse ribs and stretched longitudinally and transversely so that the thinner material fibrillates to give areas comprising a plurality of small fibres substantially uniformly distributed throughout the area.

It is proposed inter alia to use such materials as the covering layer for sanitary towels or surgical dressings. However, the small, closely adjacent, fibres, usually of a hydrophobic nature, provide some resistance to the transfer of liquid, especially nonhomogeneous body fluids, to the absorbent material beneath, and the pronounced ribs provide a certain harshness of handle.

A more recent proposal in U.S. Pat. No. 3,914,365 is to profile a sheet of polymeric material on one side with parallel main ribs and on the other with parallel tie ribs at an angle e.g. 90° to the main ribs, and thereafter to stretch the sheet to provide a net with oriented main filaments corresponding to the main ribs and tie filaments, usually also oriented, corresponding to the transverse tie ribs, leaving between them a uniform pattern of holes or voids in the sheet.

This is proposed mainly for use where its high tensile strength is of value, but also suggested for covering absorbent pads. While the uniform pattern of voids allows ready transmission of both clear and nonhomogeneous liquid, the material is rather stiff against longitudinal or transverse creasing, it being stated in that Patent that "the tie filaments are usually oriented to provide sufficient structural integrity for the network structure, tending to keep it flat and prevent folding thus maintaining the main filaments in parallel and uniformly spaced relation". Also, the material is rough to the touch, due apparently to the multiplicity of rather abrupt shoulders formed where the main and tie filaments intersect, as clearly shown in the drawings of the Patent.

We have now found that a material can be produced which in some ways resembles a woven textile material and is inherently less lustrous than previous net materials in its appearance and is considerably smoother and of finer handle, while still possessing adequate longitudinal tensile strength even at very low weights. Moreover, it can provide good transmission of clear or non-homogeneous liquid and thus can be used for example in babies diapers, sanitary towels or like structures as a cover layer.

In one aspect therefore the present invention consists in a netted material integrally formed in a synthetic polymeric material and possessing straight smooth parallel longitudinal ribs interconnected by a plurality of wholly or partly fibrillated and split strands so as to exhibit a plurality of small fibres non-uniformly interspersed with a plurality of differently sized voids, the synthetic polymeric material consisting of a blend of two or more incompatible polymers to provide a non-lustrous appearance and easy splitting of the interconnecting strands. Preferably such a net has a weight of 2 to 10 gms. per square meter, more preferably 5-8 gms.

While it is possible for the interconnecting material between the longitudinal ribs to be totally fibrous and not exhibit any visible stranding, it is also within the scope of the invention that the residual structure of the strands may still be visible. A net of this nature will generally show that the strands were originally formed to lie at an angle of up to 60° to the transverse direction, preferably an angle of between 30° and 45°.

It is particularly important according to the invention that the synthetic polymeric material is a blend of two or more imcompatible polymers. As discussed below, this increases the degree of splitting and delustres the material. Suitable polymer blends, for instance, are preferably polyolefins such as high-density polyethylene, polypropylene, or copolymers thereof, blended with a minor proportion of a polymer containing an aryl group such as high impact polystyrene. Preferably the proportion of such aryl-group-containing polymer, (such as polystyrene) by weight is not over 40%, usually not over 20% e.g. 5-20% and most preferably not over 10% e.g. 5-10%.

Such material can contain, for example, up to 5% of a inert delustering filler such as titanium dioxide. More preferably it contains up to 2% of such material. This material is added purely to improve the appearance and apparently also effects the splittability characteristics.

It is also important that the ribs are smooth, i.e. that no excrescences of material are formed or present even where any residual transverse stranding intersects the ribs.

The invention also consists, alternatively stated, in a method of producing a net wherein a film consisting of a blend of two or more incompatible polymers and provided on one side with a primary set of spaced parallel ribs and grooves at an angle of not less than 80° to the transverse direction and on the other side with a secondary set of more closely spaced parallel ribs and grooves at an angle of from 0° to 60° to the transverse direction, the combined depth of the grooves being substantially equal to the thickness of the film, is stretched by 100% to 1000% (preferably 200% to 500%) excess of its initial length in a direction at right angles to the transverse direction and by a lesser amount from 0% to 500% (preferably 200% to 400%) excess of its initial width in the transverse direction to produce a netted material integrally formed in the blended polymeric material and possessing straight smooth parallel longitudinal ribs interconnected by a plurality of split strands of non-lustrous appearance so that the area between the longitudinal ribs exhibits a plurality of small fibres non-uniformly interspersed with a plurality of differently sized voids.

Usually at least part of any transverse stretching takes place prior to longitudinal stretching.

Before stretching, the film possesses on one surface the first set of parallel straight ribs and grooves. These lie at an angle of not less than 80° to the transverse direction. Preferably they will be at 90°, or at substantially 90°, for instance at that angle produced by engraving a single-start helix around a profiling roller (multistart helices could also be used, which will increase the effective angle of the grooves to the transverse direction). Preferably packing of these primary, or first set, of ribs and grooves is from 40 to 150 such ribs and grooves per inch (16–60 per cm.).

The generally transverse ribs and grooves of the second set, on the other surface, are preferably packed at from 100 to 300 ribs and grooves per inch (40–120 per cm) and preferably lie at an angle from 30° to 45° to the transverse direction. Preferably, moreover prior to stretching the overall degree of fineness of grooving, as expressed by the average packing of the primary and secondary grooves is at least 125.

The primary (substantially longitudinal) ribs and grooves are preferably shaped to have flat surfaces to the ribs and flat bottoms to the grooves. Usually the shape of the rib is the converse of the shape of the groove, but it is conceivable that the grooves could be relatively wide whereby the ribs become more widely spaced. On the other hand, the cross-section of the generally transverse ribs and grooves (of the second set) is preferably triangular in each case, the ribs and grooves being of equivalent shape.

The net according to the invention, in the aspects defined above, is made by stretching a film. The degree of stretch longitudinally is from 100% to 1000%. More preferably the longitudinal degree of stretch is between 300 and 400%. It is found that degrees of stretch of this nature, rather surprisingly, when coupled with the use of a shaped film of an incompatible blended polymeric material as described above, draw into the longitudinal ribs the material at the intersection with the transverse strands so that the ribs feel smooth in the longitudinal direction and provide a fine handle of the material.

The material can also be stretched in a transverse direction. This will not be above 500% and usually it lies between 200% and 400%, about 200% stretch being preferred.

Such a method, and the net produced thereby represents a departure from either type of prior net as described above. On the one hand it recognises the problem of liquid transmission by providing a plurality of voids. On the other it does not attempt to alter the characteristics of the net merely by altering the type of mechanical profiling. For instance, if attempts were made to increase the number (decrease the spacing) of transverse tie filaments in the U.S. Pat. No. 3,914,365 (a) the mechanical problems of manufacturing, mounting and operating a sufficiently finely grooved roller would be considerable and (b) if they were overcome, the longitudinal ribs might be smoother — since the abrupt shoulders would be smaller — but the structure between them would be a fine uniform structure and then effectively suffer from the same problems as the other proposal.

The present invention however, is based on the surprising discovery that the stretching of a film made of an incompatible blend with primary and secondary ribs in intersecting directions gives not a simple uniform structure as might be expected from U.S. Pat. No. 3,914,365 or even such a structure with simple but uniformly fibrous transverse ribs as might be expected by combining this U.S. Patent with the disclosure of earlier U.S. Pat. No. 3,746,607 but a structure where the fibrous interconnections are irregular (of an opened-out form and the shoulders where they meet the primary ribs are either drawn into the rib or form further fibrous corner areas so as to provide a smooth handle. While it is impossible to generalise, the product of the invention will usually exhibit (a) smooth longitudinal ribs (b) more or less opened-out fibrous interconnecting strands occupying perhaps 1/5–½ the area between the ribs, (c) a plurality of voids of different sizes, non-uniformly distributed, some almost stretching from rib to rib others smaller (d) fibrous "corner" regions where the opened-out strands meet the ribs. The fibres between the ribs thus are (i) usually but not always fairly closely packed and "fanned-out" in the corners, although separate, (ii) usually but not always fairly closely packed but more parallel in whatever remains of the body of the strand and (iii) sometimes in isolated instances, but more often in bundles of two or three or some such small number, extending across the generally open interstices between strands thus defining voids of different sizes.

The invention will be further described with reference to the following Examples.

EXAMPLE 1

A typical material is made from a film embossed on one side with 100 longitudinal ribs and grooves per inch (40 per cm) each rib or groove being trapezoidal in cross-section with the longer side of the trapezium equal to its height, and on the other side with 250 grooves per inch (100 per cm) which are triangular in cross-section with an included angle of 60° and located at an angle of 45° to the longitudinal, such film being stretched 370% in the lengthwise direction and 200% in the transverse direction, and the material being 100 parts high density polyethylene to 10 parts of high impact polystyrene and 2 parts of titanium dioxide. The blend of polymer is made by mixing in the extruder barrel. The net has a weight of 6.8 grams per square meter, a smooth handle, and a generally fibrous appearance with longitudinal ribs. Under these conditions there is little or no visible transverse stranding.

Such a material is preferably made by extruding a polymer film of the blend type indicated above, usually as a molten film about 2 to 5 thousandths of an inch into the nip between two suitable rollers of approximately 6 inch diameter one containing 100 circumferential grooves and ribs per inch (40 per cm) and the other containing 250 helical grooves (at 45° helix) per inch (100 per cm) the groove shapes being as defined above. The product from the roller is solid with an overall thickness of about 5 to 8 thousandths of an inch, in that polymer becomes pressed into the grooves of the roller before being solidified.

Test results obtained using such a net were as follows, using a 32 cm. width.

|  | Dry | Wet |
|---|---|---|
| Load at break (kg/cm) | MD 0.99 | 1.02 |
|  | TD 0.045 | 0.037 |
| Ext. at break (%) | MD 15.9 | 12.7 |
|  | TD 9.2 | 6.1 |
| Tear strength |  |  |

-continued

|  | Dry | Wet |
|---|---|---|
| Along MD (g/cm) Flexural |  | 4.2 |
| Rigidity (mg/cm) | MD 36.4 TD 0.9 |  |
| Absorbency Test (Seconds) |  | 2.9 |

In the above Table "MD" signifies machine direction (i.e. longitudinal) and "TD" transverse direction.

The absorbency test was carried out by utilising the net as the cover material for a diaper, pouring on to the net 5 ml. of distilled water and measuring the time taken for the water to disappear.

EXAMPLE 2

An embossed sheet is produced at 160μ thickness by casting a hot polymer melt, comprising a blend compounded from High Density Polyethylene (Vestolen A6016 MFI 9 11 100 parts) and High Impact Polystyrene (Coles 6MW 10 parts) + 2% TiO$_2$.

The melt is extruded through a 575m/m flat die at a temperature of 200° C. at a die-gap setting of 300μ which is then embossed on both sides by casting the hot melt between two steel rollers of 135m/m dia. × 500m/m face width.

A first embossing roller is engraved on its circumference with a line pattern of grooves and ridges of 90° angle triangular cross section of 60 lines/cm × 80μ depth at an helix angle of 45° to the roller axis. A second roller is engraved on its circumference with a line pattern of continuous grooves and ridges of trapezoidal cross section at a pitch spacing of 30 lines/cm at an included angle of 15° with flats on the tops of ridges and bottoms of the grooves of 150μ at a depth of 175μ. The continuous annular-line is produced as a single start helix. Embossing of the film is carried out by casting the melt between the engraved roller pair at a pressure of 15 lbs per linear inch of working face width (2.72 kg/cm) at a casting speed of 8m/min.

Both rollers run at the same peripheral speed and are internally cooled by circulating water at 60° C. at a rate of 45 liters/min. to produce an embossed film of 160μ thickness at a base weight of 95 GSM. The cooled film is then passed into the clips of a film stretching stenter and subjected to a transverse stretch of 250% at a temperature of 75° C. and cooled before release from the clips.

The transversely stretched material is then pre-heated to 90° C. by passage over a hot roller system and fed into the roller system of a longitudinal stretching machine and subjected to a machine directional stretch of 500% at a speed of 50 meters/min. to produce a reticulate product of exceptional soft-handle at a weight of 5.82 Grms/sq.meter at a Liquid Penetration Time Constant of 2 sec. when measured to BS Specification to give the properties shown in the Table.

EXAMPLE 3

An embossed sheet is produced at 165μ thickness by casting a hot polymer sheet melt, comprising a blend of High Density Polyethylene (Vestolen A6016 MFI 9-11 100 parts) and High Impact Polystyrene (Coles 6MW 10 parts) and 2% TiO$_2$.

The melt is extruded through a 575m/m flat die at a temperature of 200° C. at a die-gap setting of 375μ. Embossing of the melt is carried out by casting into the nip formed by two contra-rotating engraved rollers of 135m/m dia × 500m/m working face running at similar peripheral speeds of 8 meters/min. at a nip-pressure of 16 lbs/linear inch of working face (2.9 kg/cm).

A first embossing roller is engraved on its circumference with a line pattern of continuous grooves and ridges of trapezoidal cross-section at a pitch spacing of 30 lines/cm with a form angle of 15° with 175μ flats on the ridge tips and the groove bottoms at a depth of 175μ. The continuous annular line is produced as a single start helix.

A second roller is engraved on its circumference with a helical line pattern of grooves and ridges of 90° included angle triangular cross-section of 100 lines/cm × 50μ depth, at a helix angle of 45° to the roller axis.

Both rollers are cooled by the internal circulation of water at 60° C. at a rate of 45 liters/min.

After embossing the cooled film is then fed into the clips of a film stretching stenter and subjected to a transverse stretch of 250% at a temperature of 75° C. and cooled before release from the clips. The transversely stretched material is then pre-heated by contact over a hot roller system to 90° and fed into the roller system of a longitudinal stretching machine and subjected to a machine directional stretch of 500% at a speed of 50 meter/min. to produce a reticulate product of exceptional smoothness and soft handle at a weight of 7 Grms/sq. meter to provide the properties in the following table.

EXAMPLE 4

An embossed sheet is produced at 165μ by casting a hot polymer sheet melt, comprising a blend of High Density Polyethylene (Vestolen A6016 MFI 9-11) 100 parts and High Impact Polystyrene (Coles Plastics 6MW) 10 parts + 2% TiO$_2$.

The melt is extruded from a 60m/m Reifenhauser Extruder through a 575m/m flat die at a die-gap setting of 300μ, which is then embossed on both faces by casting the hot melt between the nip of a pair of contra rotating embossing rollers running together at a pressure of 1 Kg/cm of working face as described in Example 3.

A first roller is engraved on its circumferential face with a line pattern of continuous annular grooves and ridges of triangular cross-section of 45° inclusive angle of 260μ pitch spacing, with a ridge flat of 100μ and a bottom groove radius of 50μ. The continuous annular line is produced as a single start helix groove.

A second roller is embossed on its circumferential surface with a helical line pattern of grooves and ridges of 90° triangular cross-section of 72 lines/cm × 68μ deep at a helix angle of 45° to the roller axis.

Both rollers are cooled by internal circulation of water at 80° C. at a rate of 45 liters/min. Embossing of the film is carried out with the follers rotating at the same peripheral speeds. After embossing the cooled film is then fed into the clips of a film stretching stenter and subjected to a transverse stretch of 250% at a temperature of 75° C. and cooled before release from the clips. The transversely stretched material is then pre-heated by contact over a hot roller system to 90° C. and fed into the roller system of a longitudinal stretching machine and subjected to a machine directional stretch of 500% at a speed of 50 meters/min. to produce a reticular product of exceptional smoothness and soft handle at a base weight of 6.5 Grms/sq. meter to provide the properties given in the following Table.

EXAMPLE 5 (Comparison)

The procedure of Example 2 was repeated using high density polyethylene homopolymer instead of the HDPE/PS blend. Results are shown below.

Results (a) The structure (the general appearance, degree of fibrillation and fibril dimensions) were examined by microphotography with scanning electron microscope.

The single FIGURE of accompanying drawing shows in enlarged form a fragment of a net produced by the method of Example 3 showing fibrillated strands 1 of relatively broken-up structure, fibrous "corner" regions 2, voids 3, longitudinal ribs 4 of smooth configuration even where they meet the strand, and occasional single or multiple long fibrils 5 extending across and dividing the voids 3.

Prior art nets based on single polymers or copolymers, i.e. not blends of polymer, do not possess such fibrous stranding 1 but a more or less solid strand with possibly one or two well defined splits in it. Also, they are generally free from fibrous corners as at 2, having instead a well defined and abrupt shoulder region forming a discontinuity or roughness on the rib 4.

The spaces between the strands are described in the prior art as being uniform. In the present invention they are non-uniform in size and shape and have the form of voids 3 defined variously by the ribs 4, fibres 1 and fibrils 5.

In practice we have found that occasionally there are fibrils in the prior art product. For example, if photomicrographs are taken of the products of Examples 3 and 5 and transected in lines from corner to corner of each cell of the net then (ignoring the fibrous corners, and ignoring the fibrillated strands since these are not transected) the number of strands otherwise extending across the cell follows the following distribution:

| No. of Strands | No. of cells Ex. 3 | No. of cells Ex. 5 |
|---|---|---|
| 3 | 1 | 4 |
| 4 | 0 | 11 |
| 5 | 3 | 10 |
| 6 | 7 | 5 |
| 7 | 7 | 8 |
| 8 | 9 | 5 |
| 9 | 7 | 0 |
| 10 | 3 | 0 |
| 11 | 2 | 1 |
| 12 | 2 | 0 |
| 13 | 0 | 0 |
| 14 | 2 | 0 |
| 15 | 1 | 0 |

This shows preliminary results with 44 measurements; more would probably remove the minor anomaly between 6- and 7-fibril cells on Example 5.

Modal value is 8 for the typical product of the invention and 4 for the otherwise similar but single polymer net.

(b) The stiffness of nets, in both machine and transverse directions, was examined by an adapted loop deflection test for determination of flexural rigidity of yarns (see Journal of the Textile Institute May 1950 T 159 "Relation between Fibre and Yarn Flexural Rigidity in Continuous Filament Viscose Yarns" by P. W. Carlene). This test is based on measuring the load to deflect a circle of material by a predetermined amount. The test was carried out by producing circles of nets from strips of 6 × 1 cm with ½ cm overlap spot bonded with adhesives. After conditioning of the specimens in standard atmosphere of 20° ± 2° C. and 65 ± 5% RH, the loops were suspended over a peg, welded to the steel rule held in vertical position and the load to produce required deflection was determined by hanging weights on the underside of loop. The flexural rigidity of the sample was calculated from the following equation:

$$G = \frac{K W L^2 \cos \theta}{\tan \theta}$$

where
G = Flexural Rigidity
K = Constant 0.0047
W = Load Mgs
L = Circumferential length of loop
$\theta$ = 493 d/L
d = Deflection mm The results are summarised in the following Table I, representing average of 5 determinations.

TABLE I

EXPERIMENTAL RESULTS
The Physical Properties of Nets

| Example | 2 | 3 | 4 | 5 |
|---|---|---|---|---|
| Polymer | HDPE/PS | HDPE/PS | HDPE/PS | HDPE |
| Rollers | 72 × 150 | 72 × 250 | 100 × 180 | 72 × 150 |
| GSM | 6.8 ± 0.8 | 6.2 ± 1.7 | 6.7 ± 0.7 | 5.9 ± 0.8 |
| Thickness-microns | 40 ± 7.5 | 48 ± 17.5 | 33 ± 2.5 | 28 ± 7.5 |
| Flexural Rigidity | | | | |
| Mgs/cm MD(a) | 35 ± 6 | 36 ± 8 | 47 ± 4 | 41 ± 20 |
| TD(b) | 4 ± 2 | 2 ± 1 | 3 ± 1 | 7 ± 1 |
| $\frac{a}{b}$ | 8.7 | 18.0 | 15.7 | 5.8 |

From the results it would appear that the ratio of stiffness in MD/TD could be used as "softness index" to distinguish between nets made from blend of polymers or single polymer. A net with "softness index" greater than 6 is thus made from a blend of two polymers embossed with axial/helical grooved rollers in transverse direction.

The degree of splitting also appears to be affected by fineness of the rollers. Softness is accentuated by the fineness of the fibrils and flattening of the fibrillated strands. Blending of two polymers reduced the flexural rigidity in T.D. of such nets by approximately half, compared with 100% HDPE. On the other hand the stiffness of the main strands in M.D. was not substantially affected by blending of these polymers.

(c) Wettability/rate of transmission of biological fluids. Attempts to measure rate of transmission of horse blood through various nets using drops of blood produced very variable results. The variability could be subjectively related to the size of holes and/or amount of fibrous material extending across the holes. A test (A50), developed for evaluation of disposable diapers was used to test the rate of transmission (penetration) of horse blood through various nets to produce Panty Pad sanitary towels for customer evaluation. In this test 2 mls. of biological fluid (horse blood) is released from a height of 2½ cms above the sample surface and the time when this quantity of free fluid sinks into the body of the sample is measured. In addition, the openness of the various nets was determined by test. This test measures the time taken by a column of glycerol 10" high and 1" diameter to pass through a sample of net. The various porosity results obtained are summarised in Table II.

TABLE II
THE ABSORBTIVE PROPERTIES OF THE NETS

| Example | 2 | 3 | 4 | 5 | Panty Pad Control |
|---|---|---|---|---|---|
| Penetration of Fluid Secs. | 1.6±0.4 | 2.8±0.3 | 3.0±0.5 | 2.2±0.7 | 2.1±0.2 |
| Porosity Secs. | 5.1±0.5 | 8.0±0.6 | 11.2±1.4 | 6.4±1.1 | 42.0 |

We claim:

1. A netted material integrally formed in a synthetic polymeric material and possessing straight smooth parallel longitudinal ribs interconnected by a plurality of fibrillated and split strands exhibiting a plurality of small fibres non-uniformly interspersed with a plurality of differently sized voids permeable to blood and water, the longitudinal ribs and the small fibres oriented by the biaxial stretching of the material and the synthetic polymeric material consisting of a blend of at least two incompatible polymers to provide a non-lustrous appearance and easy splitting of the interconnecting strands the blend comprising a mixture of a major proportion by weight of a polyolefin and a minor proportion by weight of a polymer containing an aryl group.

2. A netted material as claimed in claim 1 with a weight of from 2 to 10 grams per square meter.

3. A netted material as claimed in claim 2 with a weight of from 5 to 8 grams per square meter.

4. A netted material as claimed in claim 1, in which the residual structure of the strands is still visible.

5. A netted material as claimed in claim 1, in which the polyolefin is chosen from the group consisting of polyethylene, polypropylene, copolymers thereof and the aryl-group-containing polymer is a high impact polystyrene.

6. A netted material as claimed in claim 1 in which the polymer contains up to 5% by weight of a filler material to assist in delustring the material.

7. A netted material as claimed in claim 1 wherein the softness index, measured as the ratio of longitudinal to transverse flexural rigidity is at least 6.

8. A netted material as claimed in claim 1 in which the proportion of the aryl-group-containing polymer is not greater than 40% by weight.

9. A netted material as claimed in claim 8 in which the proportion of aryl-group-containing polymer is not greater than 20% by weight.

10. A netted material integrally formed in a synthetic polymeric material and possessing straight smooth parallel longitudinal ribs interconnected by a plurality of small fibres non-uniformly interspersed with a plurality of differently sized voids permeable to blood and water and oriented by the biaxial stretching of the material, the synthetic polymeric material consisting of an incompatible blend of at least one polyolefin chosen from the group consisting of polyethylene and polypropylene in admixture with not more than 20 percent by weight of high-impact polystyrene and being itself compounded with up to 5 percent by weight of a filler material, the netted material thereby possessing a non-lustrous appearance and easy splitting of the interconnecting strands and having a weight of from 2 to 10 grams per square meter and a softness indix measured as the ratio of longitudinal to transverse flexural rigidity of at least 6.

* * * * *